United States Patent
Goroszeniuk et al.

(10) Patent No.: US 9,308,363 B2
(45) Date of Patent: Apr. 12, 2016

(54) NEUROSTIMULATION FOR TREATING PAIN, IMPROVING FUNCTION AND OTHER NERVOUS SYSTEM RELATED CONDITIONS

(71) Applicant: Teodor Goroszeniuk, London (GB)

(72) Inventors: Teodor Goroszeniuk, London (GB); Christopher Chan, London (GB); Mark Scibor-Rylski, London (GB)

(*) Notice: Subject to any disclaimer, the term of this patent is extended or adjusted under 35 U.S.C. 154(b) by 0 days.

(21) Appl. No.: 14/340,319

(22) Filed: Jul. 24, 2014

(65) Prior Publication Data

US 2015/0012079 A1    Jan. 8, 2015

Related U.S. Application Data

(63) Continuation-in-part of application No. 12/280,042, filed as application No. PCT/GB2007/000585 on Feb. 19, 2007, now abandoned.

(30) Foreign Application Priority Data

| Feb. 21, 2006 | (GB) | .................................. | 0603464.9 |
| Nov. 10, 2006 | (GB) | .................................. | 0622457.0 |
| Oct. 2, 2013 | (GB) | .................................. | 1317485.9 |

(51) Int. Cl.
  *A61N 1/00* (2006.01)
  *A61N 1/04* (2006.01)
  (Continued)

(52) U.S. Cl.
  CPC ............ *A61N 1/0492* (2013.01); *A61N 1/0456* (2013.01); *A61N 1/0476* (2013.01);
  (Continued)

(58) Field of Classification Search
  CPC . A61N 1/0476; A61N 1/0424; A61N 1/0484; A61N 1/328; A61N 1/36021; A61N 1/0452; A61N 1/0456; A61N 1/26; A61N 1/322; A61N 2001/34
  See application file for complete search history.

(56) References Cited

U.S. PATENT DOCUMENTS

| 3,279,468 A | * | 10/1966 | Le Vine | ......................... 607/140 |
| 3,612,061 A | * | 10/1971 | Collins et al. | ................. 607/148 |

(Continued)

FOREIGN PATENT DOCUMENTS

| WO | 0236002 A1 | 5/2002 |
| WO | 0241944 | 5/2002 |

(Continued)

OTHER PUBLICATIONS

International Search Report, PCT/GB2007/000585.

*Primary Examiner* — Michael Kahelin
*Assistant Examiner* — Mallika D Fairchild
(74) *Attorney, Agent, or Firm* — Crawford Maunu PLLC

(57) ABSTRACT

Various aspects of this disclosure relate to a patch for treating a patient for chronic pain and for cosmetic treatment. As consistent with one or more embodiments, neurostimulation is carried out via stimulating electrodes and one or more reference electrodes applied externally to a region of pain (e.g., by applying current between 0.2 and 60 mA to skin). The area to be treated is located either by a stimulating device, or by using at least one of the stimulating electrodes on the device itself to locate the pain prior to treatment. The electrodes are applied to the patient's skin as located using firm pressure while a stimulating pulse is applied as treatment. This action produces a remarkable and unexpected level of pain relief over a wide area. Aspects of the disclosure extend to a method for the treatment of chronic pain using the above-mentioned parameters and procedures.

25 Claims, 12 Drawing Sheets

(51) Int. Cl.
*A61N 1/32* (2006.01)
*A61N 1/36* (2006.01)
*A61N 1/34* (2006.01)

(52) U.S. Cl.
CPC ............. *A61N1/0484* (2013.01); *A61N 1/328* (2013.01); *A61N 1/36021* (2013.01); *A61N 1/0496* (2013.01); *A61N 2001/34* (2013.01)

(56) References Cited

U.S. PATENT DOCUMENTS

| | | |
|---|---|---|
| 4,155,366 A | 5/1979 | Di Mucci |
| 4,233,986 A | 11/1980 | Tannenbaum |
| 4,498,477 A | 2/1985 | Masuda et al. |
| 4,509,521 A | 4/1985 | Barry |
| 4,510,939 A | 4/1985 | Brenman et al. |
| 4,535,779 A | 8/1985 | Ober |
| 4,541,432 A * | 9/1985 | Molina-Negro et al. ....... 607/46 |
| 4,657,023 A * | 4/1987 | Kuhn ............................ 600/392 |
| 4,907,601 A | 3/1990 | Frick |
| 4,967,038 A | 10/1990 | Gevins et al. |
| 5,449,378 A | 9/1995 | Schouenborg |
| 5,674,261 A * | 10/1997 | Smith .............................. 607/46 |
| 6,445,955 B1 * | 9/2002 | Michelson et al. ............. 607/46 |
| 6,574,513 B1 | 6/2003 | Collura et al. |
| 6,745,062 B1 * | 6/2004 | Finneran et al. ............... 600/393 |
| 6,847,836 B1 * | 1/2005 | Sujdak .......................... 600/382 |
| 6,860,896 B2 | 3/2005 | Leber et al. |
| 7,613,517 B2 | 11/2009 | Goroszeniuk |
| 2002/0151951 A1 * | 10/2002 | Axelgaard et al. ............ 607/152 |
| 2003/0191506 A1 * | 10/2003 | Shloznikov .................... 607/46 |
| 2004/0210122 A1 | 10/2004 | Sieburg |
| 2005/0267544 A1 | 12/2005 | Lee et al. |
| 2006/0015154 A1 | 1/2006 | Zou et al. |
| 2006/0052834 A1 * | 3/2006 | Goroszeniuk ................... 607/46 |

FOREIGN PATENT DOCUMENTS

| | | |
|---|---|---|
| WO | 03004093 | 1/2003 |
| WO | 2005110531 | 11/2005 |
| WO | 2007096600 A1 | 8/2007 |

* cited by examiner

FIG. 2A
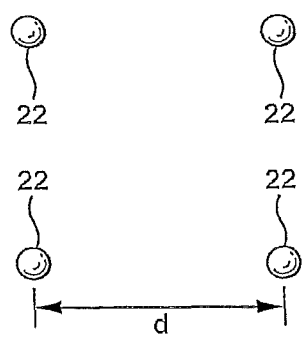
FIG. 2B
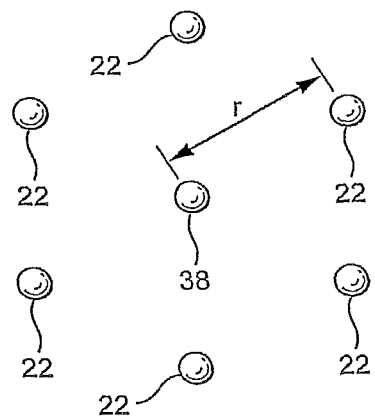
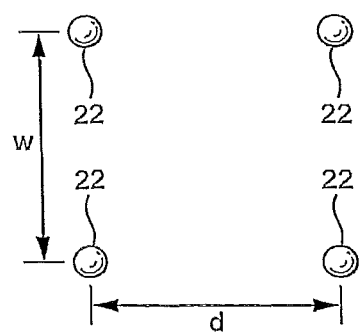
FIG. 2C

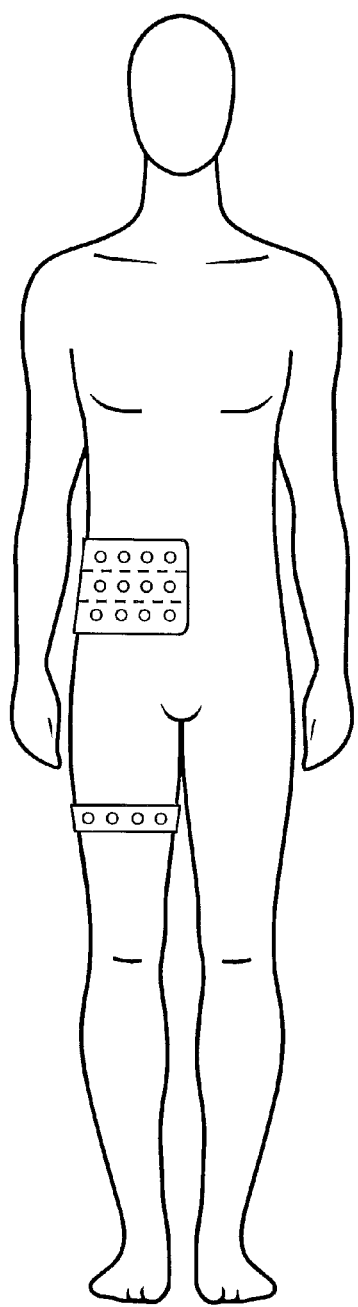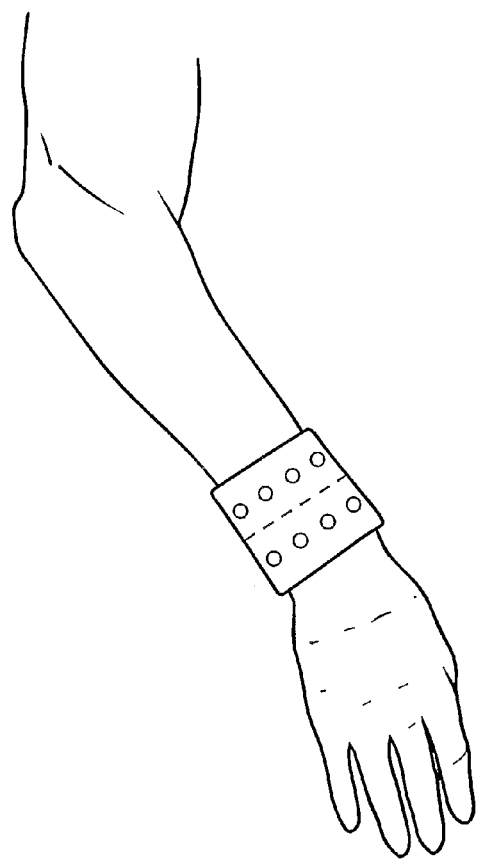
FIG. 10A
FIG. 10B

NEUROSTIMULATION FOR TREATING PAIN, IMPROVING FUNCTION AND OTHER NERVOUS SYSTEM RELATED CONDITIONS

Various embodiments relate to improvements in and relating to devices for treating acute and chronic pain, for cosmetic applications, relieving diseases that aetiologically have a functional or neural component, including gastrointestinal, rectal, urological, gynaecological, musculoskeletal, endocrine and nervous system disorders, to include malignant conditions. Such conditions and disorders will be referred herein and hereafter as 'the Specified Conditions' and various embodiments are described in this context. However, it should be understood that one or more embodiments are applicable to implementation with other treatment approaches and uses.

Peripheral Neurostimulation [PNS] is the fastest expanding area of Neuromodulation and is gaining in popularity as a treatment of chronic pain and recently as application for an improvement of function. Traditionally such neurostimulation has relied on the implantation of a device in a position adjacent to the nerves supplying an affected area or targeted at the site of pain. An electrical stimulation is applied to implanted electrodes to achieve a level of relief in the patient. However, such devices need to be accurately located and generally require a small surgical procedure in order to implant the device. The procedure is carried out by a trained medical practitioner or specialist. The transcutaneous stimulation [TENS] is very popular but its effectiveness has been frequently challenged. New forms of different modes of External Stimulation are emerging rapidly with improved technology reaching many new targets.

U.S. Pat. No. 5,449,378 (Scouenbourg) describes a device for relieving chronic and acute pain, which includes a shapable electrode plate through which a plurality of electrodes are fixed and terminate, at their respective free ends, in pointed electrode tip portions for skin penetration. The electrodes are connected to a control unit designed to activate the electrodes. When pressure is applied, the electrode tip portions are designed to penetrate the isolating outer layers of the epidermis to stimulate the receptors of the skin while electrical stimulation is applied as in acupuncture.

U.S. Pat. No. 7,613,517 (Goroszeniuk) describes a device for the treatment of chronic pain by electrical neurostimulation comprising a pair of electrodes and an electronic power supply arranged to supply a pulsed signal between the electrodes which are arranged, in use, to be pressed firmly onto a patient's skin both accurately to locate the source of pain in response to a locating pulse and then to remain in place as located to treat the pain by applying an appropriate stimulating pulsed signal transcutaneously to treat the pain.

An embodiment is directed to applying and maintaining firm pressure to a stud or studs in order to enhance the delivery, penetration and the distribution of electrical stimulation to required targets externally without skin penetration in the aim to treat the Specified Conditions, pain, with the option, when it is practical, to apply electrical stimulating pulses to the stud or studs to enhance the relief.

Various embodiments are directed to specific patches for applying sustained pressure to a single or to multiple stud electrodes adapted to be applied to various parts of the anatomy, and to applying electrical stimulating pulses to the stud(s) in order to treat the Specified Conditions.

A patch for treating the Specified Conditions in accordance with one or more embodiments comprises a firm, inelastic or semi-elastic, insulating support having one or more rounded or substantially hemispherically- or parabolically-shaped electrically-conducting metallic studs projecting from one side of the support, which support is arranged in use to be held firmly against a patient's skin by mechanical means as herein defined so that the studs indent the patient's skin, the studs being arranged for connection to a power source and a generator of electrical stimulating signals which in use apply stimulating signals to the patient's skin whilst pressure of the studs on the skin is maintained.

In this specification and the attached claims 'mechanical means as herein defined' shall mean any one or a combination of the following:
 elastic or inelastic straps or the like, e.g., polymeric straps, forming a part of the support or attached to it and arranged to be attached around a patient's limb or body;
 A hook and loop fastener such as Velcro (Registered TM—3M Corp. Inc.), or the like, patches on the support and arranged to hold the support firmly around a patient's limb or body part;
 an adhesive coating arranged to allow the support to be removably stuck to a patient's skin so that the stud(s) are pressed firmly into the patient's skin; or
 a shaped or formed element arranged to fit tightly over a part of the body by stretching or strapping it in position,
in each separate case the said mechanical means being arranged to hold the support firmly against the patient's skin so that the studs are pressed into the patient's skin.

Electrical stimulation via the studs is an essential element of the treatment in order to achieve optimum results, though some relief may continue to be felt by a patient once the electrical stimulating signal has stopped due to the acupressure effect of the pressure of the studs on the patient's skin. Such relief may justify that the device remains in place between treatments with the appropriate electrical stimulating signals.

In some instances, the treatment not only provides significant relief over prolonged periods, but also has the additional benefit of improving function.

The fact that the electrodes are arranged to be applied externally for non-invasive use permits the device to be used and, to a certain extent, controlled by a patient himself, although the initial set-up of the device will be performed by a medical practitioner or specialist. The very low current which has been found to be effective on many patients allows the device to be manipulated safely by older people—the most frequent sufferers from chronic pain—or even by children or people who are handicapped without endangering them or exposing them to discomfort.

Other embodiments are directed to a method for treating the Specified Conditions using substantially hemispherical or parabolic studs projecting from the patch that is pressed and held against a patient's skin by the said mechanical means so that the stud electrode(s) cause a depression or depressions in the skin, and applying a stimulating signal to the studs substantially as described and claimed herein. Certain method-based embodiments relate to the frequency, duration and current of the electrical stimulation as applied to the studs.

Various methods extend to locating the studs using an electrical stimulating or locating device that is used to determine the area to be treated for optimum effect prior to applying the studs.

The patch is most effective when the stimulating electrodes comprise substantially hemispherical contacts which project in such a way that they can be applied to an affected area with sufficient pressure that they produce small indentations in the skin. The patch comprises electrodes that may be mounted on a non-conducting, semi-rigid support or supports. The firm pressure, sufficient to produce small indentations in the skin, together with the stimulating signal contributes significantly to the effective treatment of the pain or treatment of the Specified Conditions.

Each stud may have a substantially hemispherical or parabolic shape with a diameter of 3 to 12 mm in diameter, or between 6 and 8 mm in diameter. In some applications smaller electrodes 4 to 6 mm in diameter are desired, for example to provide a higher density of electrodes. In areas where a more generalised relief is required, larger studs of diameter between 8 and 12 mm may be implemented. As the studs are substantially hemispherical or parabolic in form, their height (from their base to their apex) is equal approximately to their radius or optionally 1 to 2 mm more.

The studs may additionally have, or be formed integrally with, surrounding washers that enhance the degree of support and firmness by which the studs may be applied to a patient's skin. Alternatively, the surrounding washers may be formed of a plastics material and attached solidly to the studs.

The diameter of supporting washer or backing plate where required will generally be up to two or three times the diameter of the studs, say, 15 to 30 mm, or 20 to 25 mm in diameter. It may equally be of a substantially elliptical, square, hexagonal or octagonal shape as may be dictated by the required application.

The studs need to be capable of transferring an electrical stimulating signal to the patient's skin, and therefore in most cases will be metallic, often plated for appearance or protection. However, the ability to coat plastics with a metallic coating to produce an electrically-conducting surface allows the studs optionally to be made of a plastics material. Whilst the studs must have a non-penetrating, generally-rounded surface that abuts the patient's skin, there is no restriction as to their shape, disposition, arrangement on a support, except as required to treat the affected area of a patient, be it large, small, elongated or otherwise, and the density of treatment called for by the physician or specialist.

For rectal, urological, gynaecological and other applications where the studs may be in contact with more delicate tissue, they may be of a shallower and more rounded shape. In such applications they may not need to indent the skin as much in order to make a satisfactory electrical contact. These studs may conveniently have a diameter of 8 to 10 mm, but have a reduced height (base to apex) of 3 to 5 mm. Plastics studs with a conducting surface coating may be preferred in this application, being potentially softer and having some flexibility.

In all applications it may be helpful or necessary to apply a silicone gel or similar product to assist in producing a satisfactory electrical-conducting contact with the patient's skin.

The patch advantageously comprises means for electrically connecting some or all of the studs as electrodes to a stimulating signal generator for producing a stimulating signal or series of pulses for the treatment of the pain by means of transcutaneous electrical stimulation. Generally the parameters of the stimulating signal will be set by a physician or specialist so that the patient has no or only limited ability to alter the stimulating signal in amplitude or frequency once they have returned home. The positioning of the stud electrodes may additionally be selected or adjusted by means of the patient's response to a stimulating device, or simply by careful manipulation of the device over the selected area whilst applying a stimulating signal until optimum relief is achieved.

The stimulating parameters are thus set by a physician or specialist who allow room for the patient to switch the electrical stimulation on and off, within permitted limits, and to make small adjustments to the frequency, pulse duration and amplitude as pre-set by the physician.

Whilst the electrical stimulation is generally applied for a limited time, often between five and 20 minutes, by retaining the studs in place with the applied pressure has been found to enhance and prolong the relief. This may be particularly useful for injured athletes wishing to train or compete in spite of an injury. In such cases it may not be practical (or indeed even permitted) to apply the electrical stimulation during exercise, though a patch with one or more studs that apply pressure to the skin, muscles and or nerves may be possible. Nevertheless, for some patients it may be necessary for the treatment to be longer, intermittent or even continuous or substantially continuous on a 24 hour basis.

This electrical stimulation, either intermittently or continuously, combined with the pressure applied to the studs provides in most cases very successful relief of acute and chronic pain and the Specified Conditions.

The patch may be shaped, sized or formed in a way that is best adapted to the Specified Condition to be treated. In its simplest form the patch conveniently comprises several juxtaposed perforated adhesive strips each of which has a number of studs arranged in a line or in any other desired pattern. The patch may be used either as a single unit having a relatively large number of stud electrodes to cover a large area or it may be cut or torn into single or multiple strips as desired and optionally stretched appropriately to fit over a part of a patient's body. Studs may be chosen or activated to correspond with specific locations on a patient that can be identified by a practitioner by using a stimulating device. In this way a very effective treatment may be achieved without activating ineffective electrodes, thus prolonging the life of the power source. Studs on adjacent strips may be operated in association with each other or independently.

Alternatively, the patch may be provided with a strap which allows it to be attached and held in place on a patient. This is particularly useful where the arm, wrist or chest is to be treated.

Various other forms may be designed to suit the various sites to be treated. Patches in the form of collars, bracelets, bands or belts are particularly useful in that they can be held firmly in place around a limb, neck or torso. The patch may otherwise be incorporated into or comprise a cap, glove or sock to treat a specific location. A larger number of electrodes may be incorporated into such items permitting them to be standardised, albeit in practice only the required number of specific electrodes may be activated in use on a particular patient.

Specific forms may be shaped and adapted specifically to treat rectal, urological and gynaecological pain; such patches may require softer or flatter studs to avoid the device causing discomfort in itself.

In another form, the electrodes may be mounted on the patch which comprises a semi-rigid plastic support or is formed of a substrate that may be cured to conform to the area to be treated. The support may be curved to conform to the body part to which it is intended to be applied so that pressure can be applied equally to all the studs. For instance, the support may be curved to conform to skin surfaces of a patient that are differently aligned such that different studs are presented at different orientations to respectively contact different portions of the skin (e.g., around different portions along a curved surface of a shoulder).

In some instances it may be helpful to encase the patch in a shell which may comprise a casing provided with foam or fabric liner or sleeve in order to more comfortably adapt it to the patient's anatomy, and to provide the desired level of pressure on the electrodes. This may be particularly well adapted for treating an ankle injury, an amputation or a wrist or other limb injury or associated chronic pain, or to improve function.

Whilst a number of different applications have been alluded to, various embodiments involve a pre-formed patch having an array of electrodes adapted to fit the area to be treated and to treat the localised pain.

The patches may be supplied as fabric, elasticated or plastic bands of different shapes, and may form an integral or replaceable element of the item. They may be coloured to dissimulate them, or be decorated or coloured as a fashion item, or to distinguish them as a trade mark. The studs may even be incorporated into bijouterie, e.g. for facial or cranial stimulation. Such may be suitable for covering, dissimulating or making the electrical stimulating device effective, though discrete and less evident to third parties.

The patch may thus be adapted and formed with stud(s) placed appropriately to treat any of the Specified Conditions.

In use the studs are kept in firm contact with the patient's skin, without penetrating it, either by such mechanical means such as an adhesive on the underside or stud side of the support, or the straps or such mechanical means as herein defined that hold it in place or due to the stretch of the fabric that it is made.

In another embodiment the stud array is mounted on the patch that comprises a semi elasticated fabric having an adhesive surface on the side of the studs so that in use the insulating support can be stretched over the patient's skin in the area to be treated and held firmly in place by the adhesive so that the studs are held firmly against and exert pressure on the patient's skin. Such an adhesive elasticated strip may be cut to the desired length and stretched and stuck over a painful muscle, nerve or tendon, on the leg or arm, for example following an injury or surgery.

Many adhesive coatings are presently available, but where a backing plate or washers are provided surrounding the studs, the washers reinforce the pressure applied by the patch to the studs, so that a less tactile or aggressive adhesive may be employed. In some instances the patch may be reusable by following the simple precaution of covering the adhesive with a suitable substrate when not in use.

Alternatively, the patch may be attached and held firmly in place by means of a Velcro (Registered TM—3M Corp. Inc.) or similar backing which 'grabs' the patch.

Where the patch is intended for re-use, for example where it is specifically formed to fit an arm, leg or joint and is more costly to manufacture, it may conveniently be held in place by mechanical means comprising one or more plastic or elastomeric straps, so that it can be washed, and sterilized if necessary.

The mechanical means will be chosen according to the site and condition to be treated, and probably influenced by cost considerations. It may comprise one or a combination of the suggested means above.

When the pressure is applied by means of the support the rounded tips of the studs are purposely designed to apply a specific pressure so as only to depress or indent the isolating outer surface layers of the epidermis so as to stimulate the receptors of the skin, though not through penetration.

In some embodiments, a number of stimulating electrodes are used to treat an extended area. There may be between 2 and 24, though generally not more than 16, stimulating electrodes whose centres are between 50 and 150 mm apart. In many implementations there are 4 to 6 stimulating electrodes with an enclosed area of 150 to 200 $cm^2$. For treatment of the back or spine, however, 16 electrodes may be implemented, arranged in 8 pairs and covering up to 1000 $cm^2$.

When electrical stimulation is applied the combination of electrical stimulation and the firm pressure on the stud electrodes has been found in many cases to produce a significant relief of the pain that has been targeted, that may endure for hours, if not days. The electrical stimulation may be low frequency, e.g. 1 to 50 Hz, or high frequency, e.g. 5 to 10 kHz, depending on what works with the particular patient and their condition. At present frequencies of 2 to 10 Hz are implemented in many applications, though some conditions are found to respond better to high frequency stimulation of 5 to 10 kHz.

The patch is provided with a terminal for connecting it with an external stimulating device. However, as electronics and power sources improve and become smaller and cheaper, in a particular embodiment the signal generator and the power source form part of the patch or may be removably attached to it or arranged to clip onto the terminal that has been provided for a hard-wire connection.

Where the stimulating unit is provided on the patch, it may conveniently incorporate a radio frequency transmitter so that the stimulating parameters can be set and modified either by using stimulating unit equipped with a suitable transmitter. Alternatively, the parameters can be set and controlled by an RF link with a computer, tablet or smart phone using an appropriate application. Such external means for controlling the device by means of an RF link will be referred to herein in the specification and claims as external control means as herein defined.

The patch may effectively be self-contained and can be left in place without wires. It may even incorporate a timer so that it applies a stimulating signal at pre-arranged times to treat persistent pain.

This combination of firm pressure together with the electrical stimulation provides a surprising level of relief comparable to that achieved by a percutaneous implant. Furthermore the multiple electrodes extend the relief over an area which is simply not feasible using any other known method.

In a recent trial, in more than half the patients on which the device was used, the Visual Analog Scale (VAS) pain score was reduced to 0 over a period of five minutes.

Various manufacturing techniques may be used to place the studs suitably on the patch. The studs may be placed through the fabric incorporating an internal electrical conducting means arranged to make electrical contact with the desired electrodes on the support. This may be in the form of a conducting strip, band or web formed of an electrically conducting material. The stimulating electrodes may thus be selectively riveted through the insulating support in such a way that they make contact with the electrical conducting means. Alternatively, the insulating support may be provided with pre-formed holes adapted to receive the electrodes in such a way that they make electrical contact with the electric conducting means disposed within the insulating support.

An electrical reference or earthing signal may be applied to the patient's skin either through a conducting silicone patch, or by connecting one or more of the studs to the reference signal or by incorporating an earthing patch on the patch itself for the reference signal.

In another embodiment selective bands of conductors within the insulating support are arranged respectively to carry a stimulating signal and a reference signal so that stimulating electrodes are in electrical contact with a stimulating signal and reference electrodes are in contact with a reference signal. In such an arrangement the polarity of the studs may be maintained or selectively changed as found to be most appropriate for the treatment.

Specifically the physician or specialist may select either the standard diameter studs (8 to 10 mm in diameter), or the smaller studs (5 to 6 mm in diameter) for more sensitive areas or where a higher density of studs is required. As mentioned above for rectal, urological, gynaecological applications the flatter studs may be chosen for reasons of comfort and practicality.

One or more light-emitting diodes (LEDs) may be included on the outer surface of the support. These are included in the electrical stimulating circuit so that they light up when a stimulating signal is applied to the circuit. Where several discrete circuits are present, supplying different studs or groups of studs, LEDs may be included in each circuit; if desired, differently coloured LEDs may be used.

Various aspects of the disclosure involve accurately locating stimulating electrodes with respect to an affected nerve, plexus or non-specific target area using a locating stimulator or the stimulating device itself in its locating mode. In addition each stimulating electrode has a hard, rounded end, generally at the end of a rigid stem, which can be 1) applied firmly to the skin in the affected area as located either by the device in a location mode or by a separate nerve locator, and 2) moved in response to the patient's reaction to the stimulating signal applied to the stimulating electrodes further to fine-tune the treatment.

The stimulating signal is advantageously applied to different electrodes or pairs or selected groups of electrodes alternately, sequentially or in rotation to improve the level of relief to the patient, and the power supply is conveniently arranged to offer this feature. This also has the advantage of reducing the current density at the reference electrode(s) and the overall required power output of the power supply.

The stimulating signal applied to each electrode may be applied sequentially with such a short delay between each electrode that it is indiscernible by the patient that not all the electrodes are activated simultaneously.

In general the stimulating electrodes will be anodes (+) with the reference electrode being the cathode (−). However, some patients find that inverting the polarity produces greater relief and thus the polarity can be selected by the specialist accordingly.

The energy required for the treatment may depend on the size of the nerves (large, heavily myelinated A α motor fibres at one extreme versus smaller unmyelinated C fibres at the other). Thus the energy delivered E (energy in nC)=I (current in mA)×t (duration in μs). In a typical example, a pulse may last from 0.05 ms to 1 ms and the applied current may be from 0.5 mA to 60 mA. In practice the highest currents would not be used with the longest pulse widths, so that the power per pulse would not be likely to exceed 50 mC and would be more likely to be in the order of 15 to 25 mC or less for a tender part of the body.

In order to obtain the necessary transcutaneous current a relatively high voltage—up to 85V, though more traditionally 65V—may be required. The pressure that can be applied by the stimulating electrodes (and by the other, reference, electrode) to the skin allows the voltage to be reduced because of the lower resistance, making burning less likely. The provision of rounded ends of the electrodes also acts to distribute the current more accurately and evenly than would be achieved by a traditional silicon carbon electrode. A gel may be used to enhance the conductivity between the reference electrode and the skin.

In other embodiments one of the electrodes, the reference electrode, may comprise a silicon-carbon patch connected to the power supply and is arranged to be stuck to the skin close to the affected area. In order to avoid an excessive current density at the point of contact with a patient's skin, the area of the reference electrode may be greater than that of a single stimulating electrode if more than a single stimulating electrode is likely to be operated simultaneously.

Additionally, the power supply is arranged so that if one or more of the electrodes or pairs of electrodes does not make proper contact with the patient's skin, the current is accordingly reduced to prevent discomfort or even burning which might otherwise occur. This external approach, whereby the electrical impulse is applied externally over the nerves, plexuses and at non-specific areas in a non-segmental distribution, produces results which are overwhelming. Pain relief can be compared to the percutaneous direct approach, with results of the same magnitude of 70-100% pain relief achieved as measured on a VAS score.

The duration of the pain relief following a typical 5 min session where the electrodes have been placed correctly can vary between minutes or hours and days or even weeks.

One of the most important components of this novel approach to peripheral neuromodulation in treatment of neuropathic pain is the frequency of the stimulation, which is contrary to established recommendations. The frequency may be effective in the range of stimulation 1-50 Hz, or between 2 and 10 Hz or up to 50 Hz.

The stimulating unit may thus be set to provide a specific current at each stimulating electrode of between 0.2 mA and up to 15 mA, though not to exceed 60 mA. Optimal results appear to be achieved when the applied current to each electrode is between 2 and 10 mA or 15 mA. When used in a dermatomal target field area the current may be up to 20 mA. The current combined with the pulse width determines the level of energy applied. The pulse width may be from 0.05 to 1 ms. The penetration of the signal increases with the pulse width while the applied current may be increased at shorter pulse widths.

The current is set by the practitioner according to the pain, the patient's skin and the part of the body to be treated with an objective to use the lowest current consistent with achieving the desired relief and without causing discomfort or burning. Clearly more delicate parts of the body, for example around the eyes, or more fragile skin will require the current and power to be limited accordingly.

Once the stimulating electrodes have been accurately located the current can be reduced in most cases and the frequency can be adjusted to achieve the optimum level of relief. Accurate location of the electrodes thus reduces the discomfort to the patient and the risk of burning. It also prolongs battery life for a portable unit.

For maximum effectiveness the electrodes are accurately positioned using a stimulator-and-location mode prior to treatment. Thus, the stimulating unit may first be used to position the treatment electrodes prior to fine-tuning the treatment current and frequency. The power supply may then be adjusted and used to provide the desired electrical output to the electrodes for the treatment.

As it may not be necessary to carry out the location procedure on each occasion, either a separate nerve stimulation function on the device may be used by the specialist practitioner who prescribes the treatment or a separate locating stimulator may be used. In normal use the location function is switched off so that the patient is not confused. The treatment parameters equally may be pre-set or pre-limited to prevent the patient from harming himself by mistake.

The diameter of the contacts of the electrodes will depend on the muscle, nerve type or area to be treated. They may be between 4 and 12 mm long or in some cases up to 20 mm, but generally 4 to 8 mm.

Some embodiments are directed to treating a patient for chronic pain or for cosmetic treatment by neurostimulation comprising applying a plurality of electrodes externally, i.e., to the surface of the skin, in the region of the pain, applying firm pressure to the electrodes and passing a low frequency current between one or more reference electrodes and the stimulating electrodes.

External multiple neurostimulation in accordance with one or more embodiments results in improved relief of chronic neuropathic pain, an improvement in peripheral circulation, improved mobility and function, and improved sensory perception. It has the great advantage that it can be applied by the patient him/herself when required and as often as they wish with little or no adverse effects. As no surgical procedure is required, treatment can be easily be modified or stopped if it fails to produce the desired relief or if it causes an unwelcome response.

Additionally, it can be used in conjunction with traditional analgesics or implants either to complement the relief or if the site of the pain moves. This is particularly useful in the treatment of non-specific or non-segmental pain.

Aspects of the invention will now be further described by way of example with reference to the accompanying drawing in which.

Figure 3A:
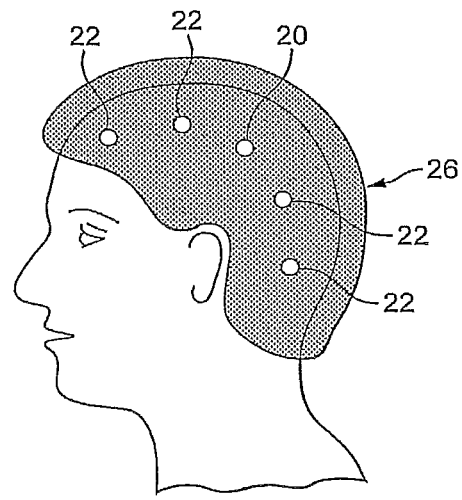
Figure 3B:
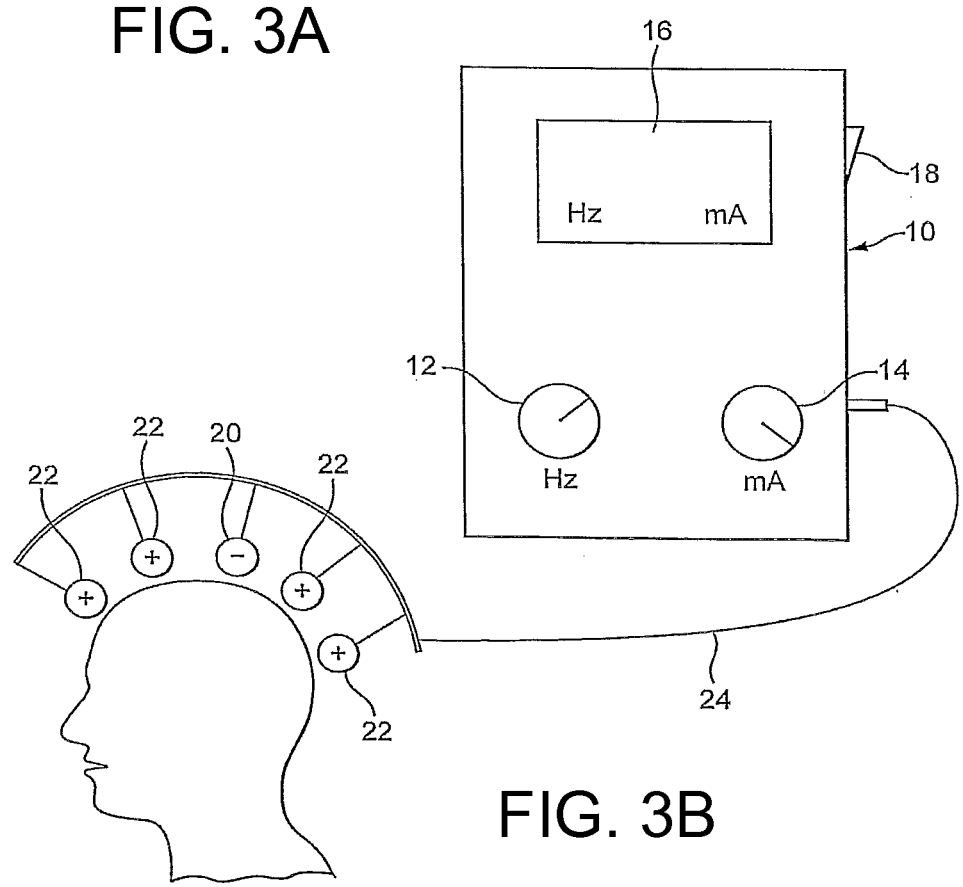
Figure 4:
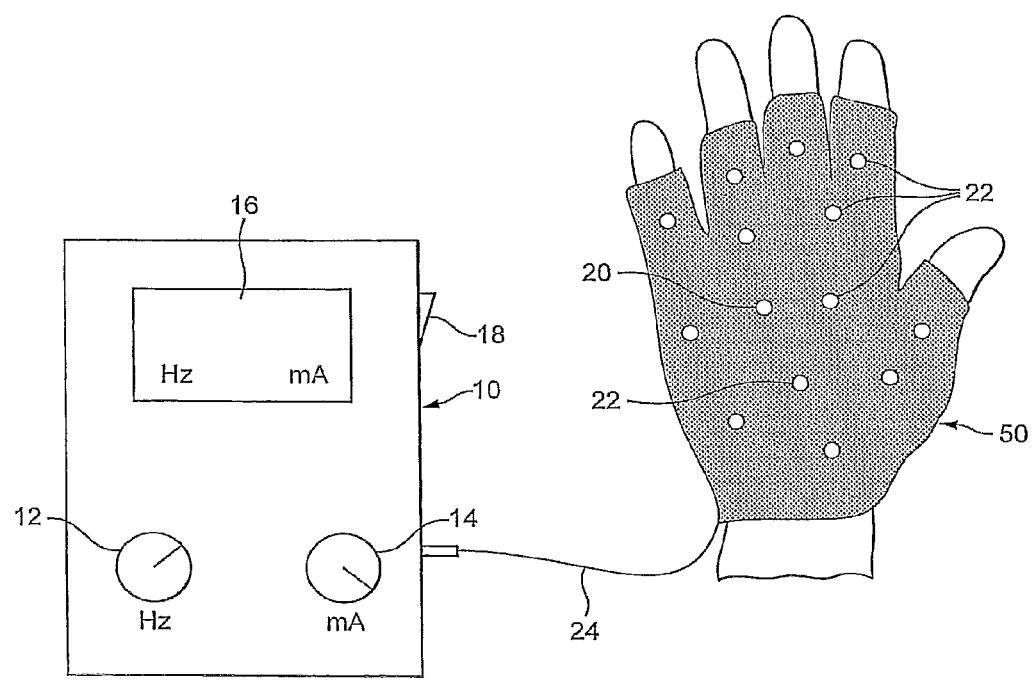

FIG. 2 A to C illustrate three different geometric arrangements of clusters for stimulating electrodes for use with the device;

FIGS. 3A and 3B illustrate diagrammatically a cap or headpiece fitted with electrodes;

FIG. 4 shows diagrammatically a glove fitted with multiple electrodes; and

Figure 5:
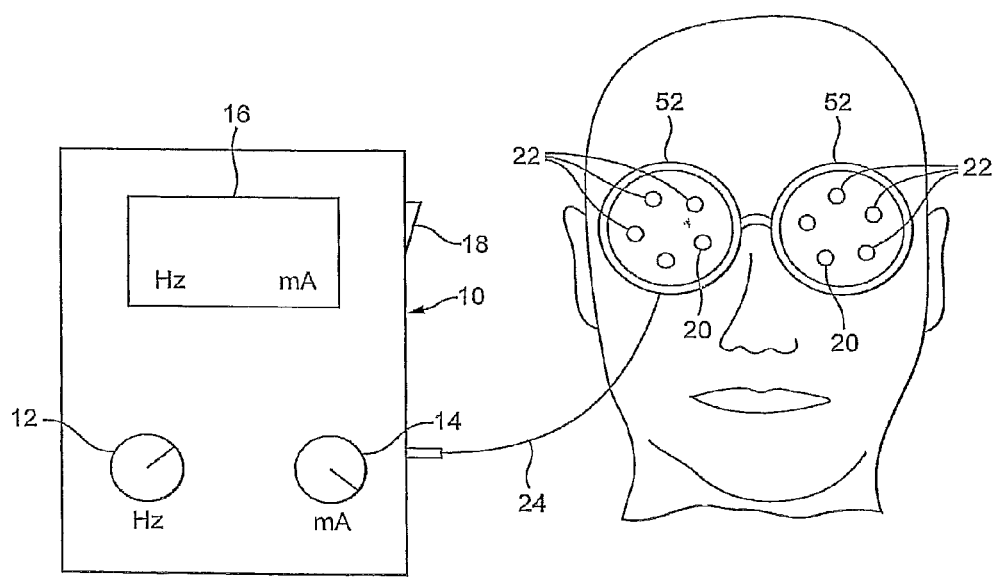

FIG. 5 shows diagrammatically a pair of eye patches fitted with electrodes.

Figure 6A:
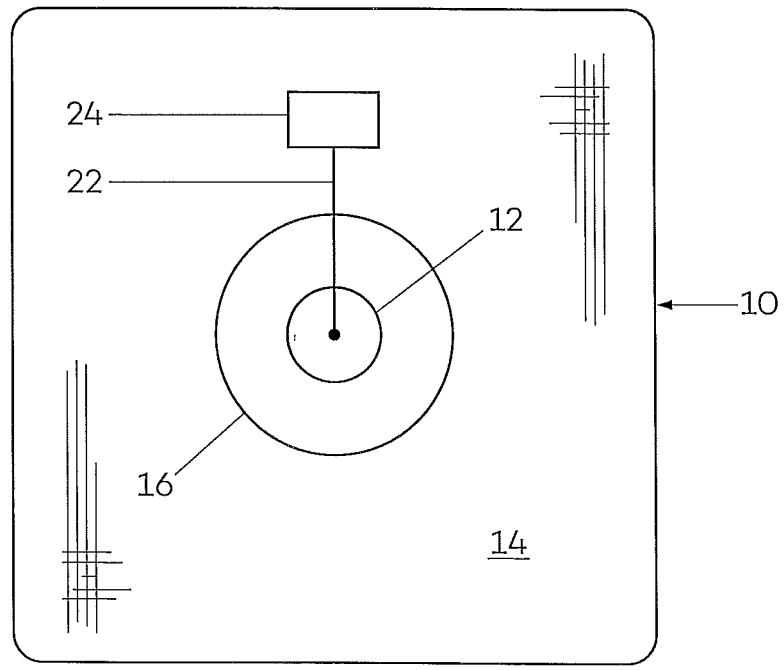
Figure 6B:
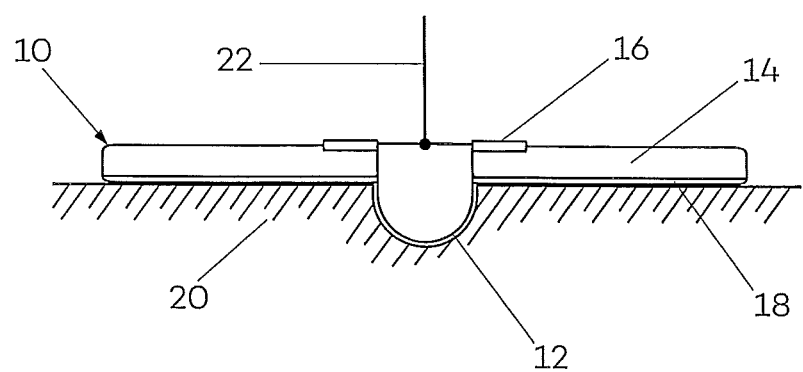
Figure 6C:
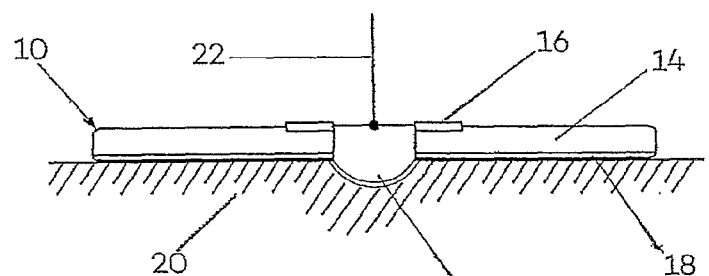
Figure 7D:
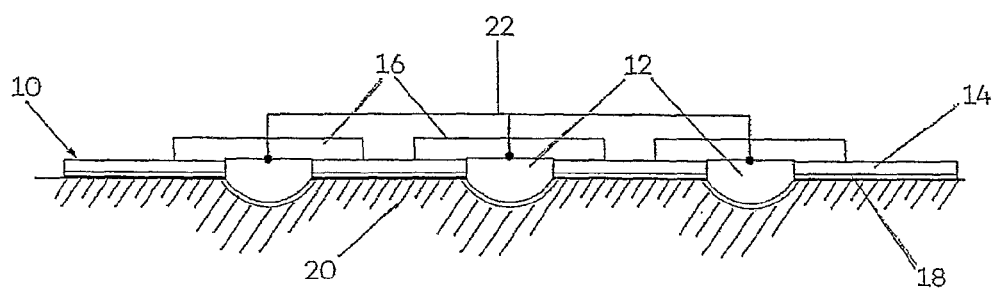
Figure 7A:
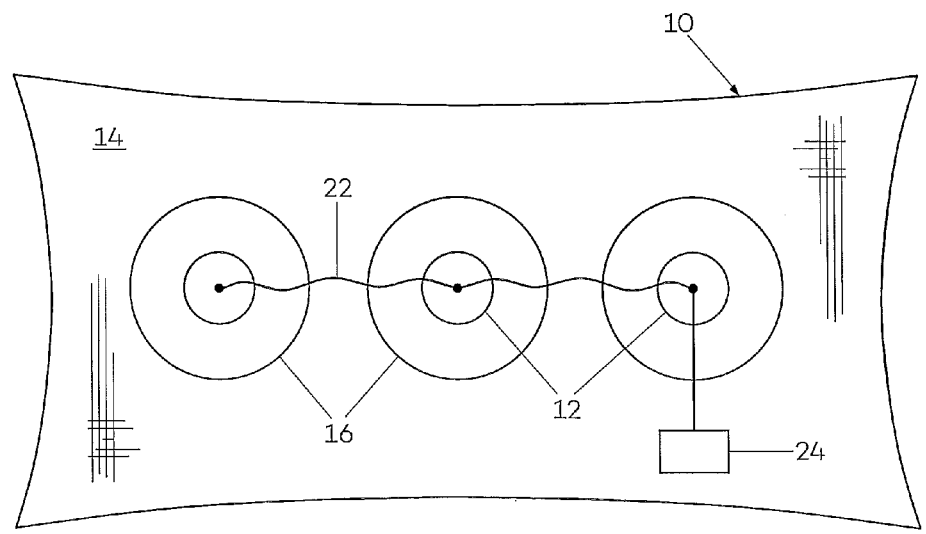
Figure 7B:
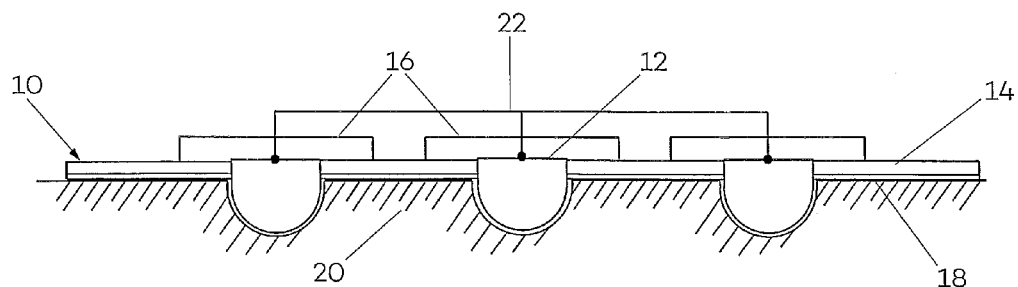
Figure 7C:
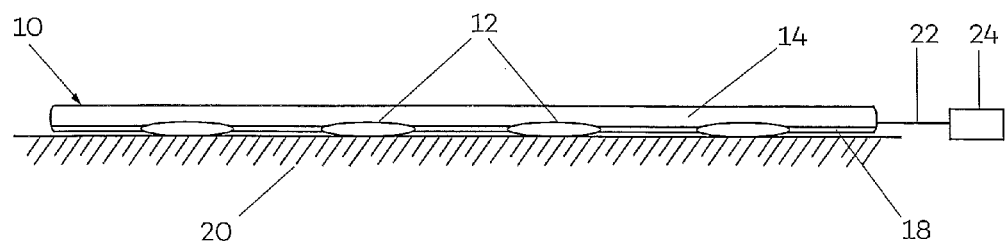

FIG. 6A illustrates a patch for treating the Specified Conditions which comprises an adhesive support having a single stud that can be adapted in form and size to be attached to a patient;

FIG. 6B shows the patch in FIG. 6A in cross section in use applying pressure to a hemispherical stud showing an indentation in a patient's skin;

FIG. 6C shows the patch in FIG. 6A in cross section in use applying pressure to a rounded stud showing the indentation in a patient's skin:

FIG. 7A is similar to FIG. 6A but shows a patch having a plurality of studs;

FIG. 7B is similar to FIG. 6B, and shows the patch attached and applying pressure to studs with a hemispherical distal end applied to and making an indentation in a patient's skin;

FIG. 7C is a side view of a patch having studs suitable for rectal, urological, gynaecological applications;

FIG. 7D is side view similar to FIG. 7B of a patch having rounded studs.

Figure 8:
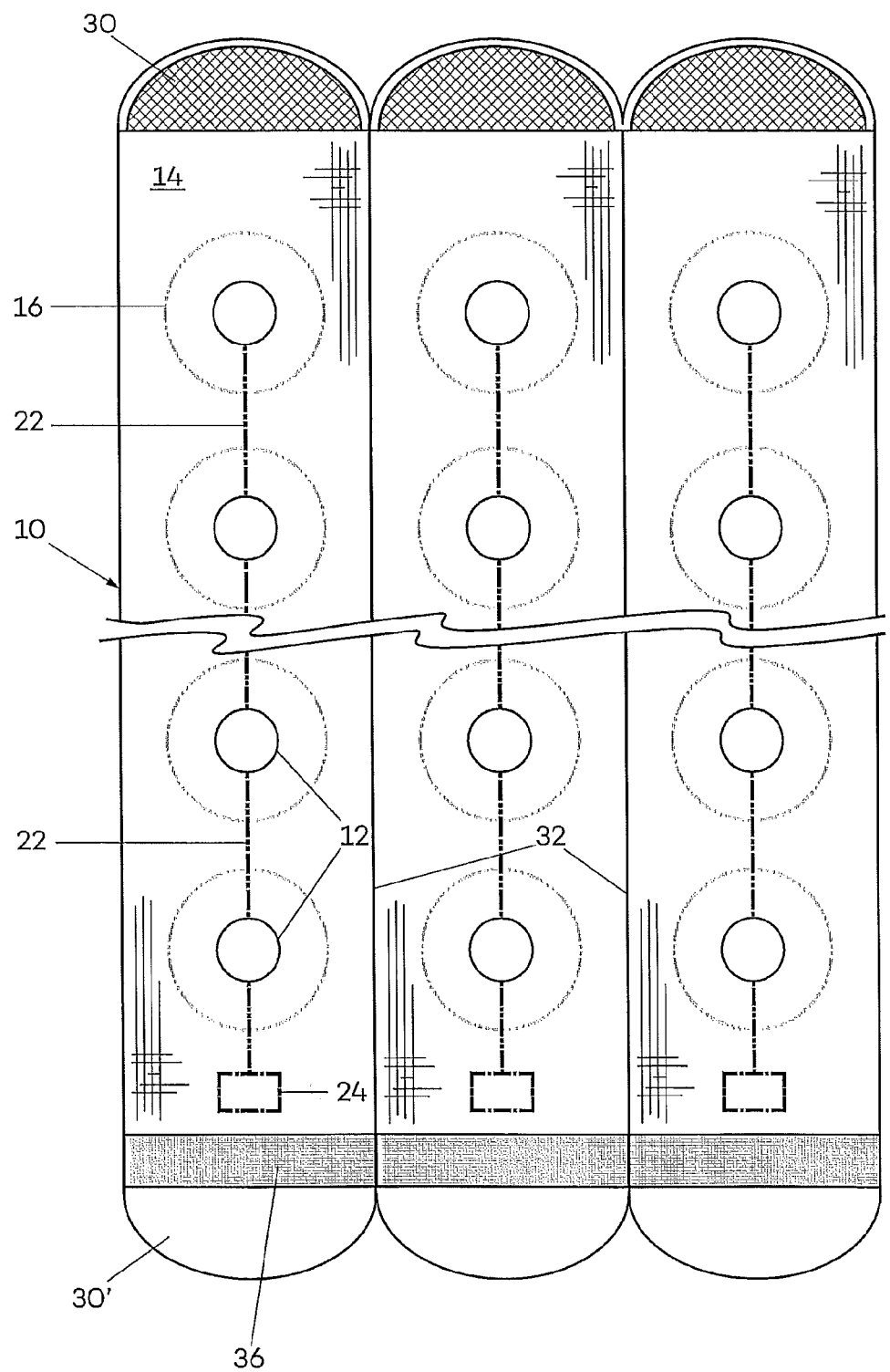
Figure 9A:
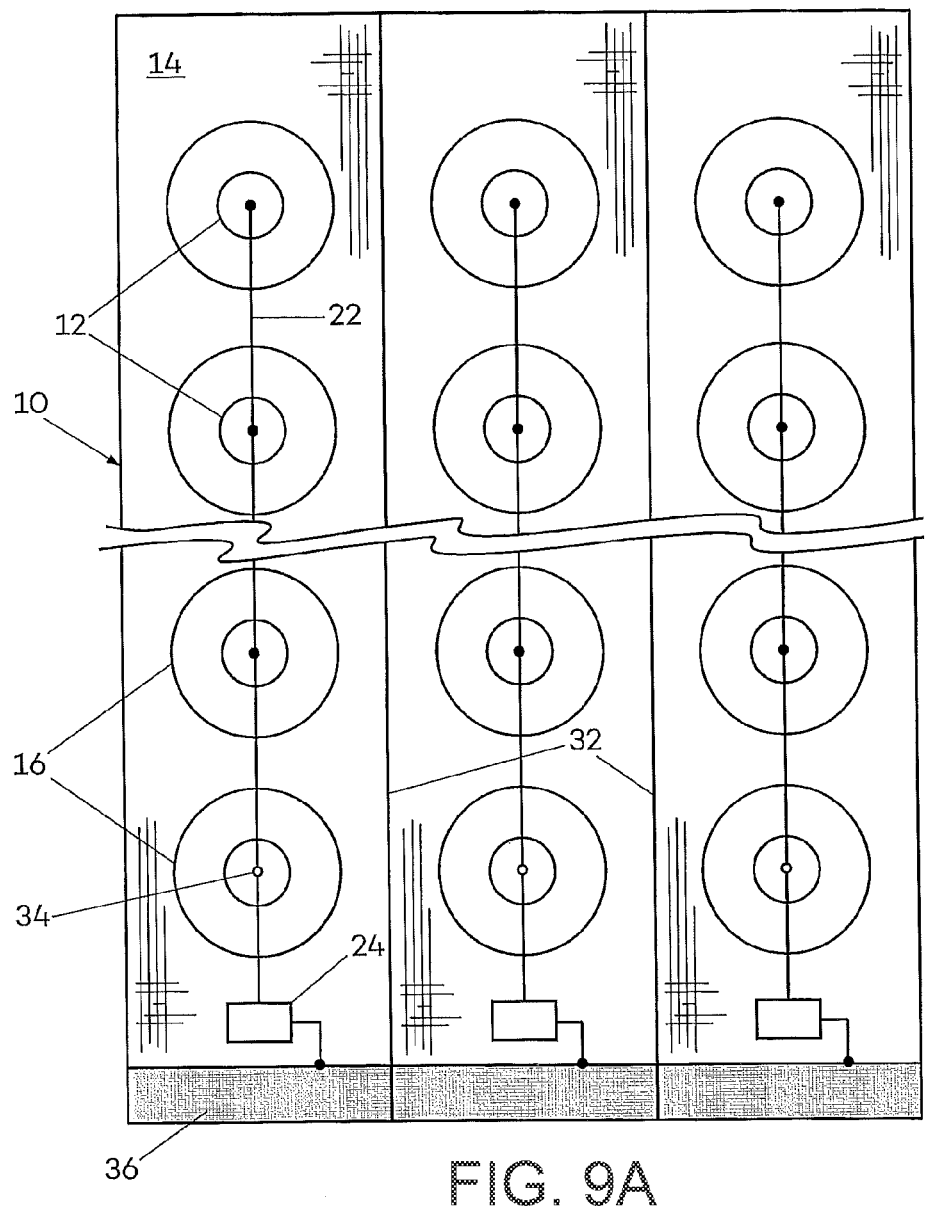
Figure 9B:
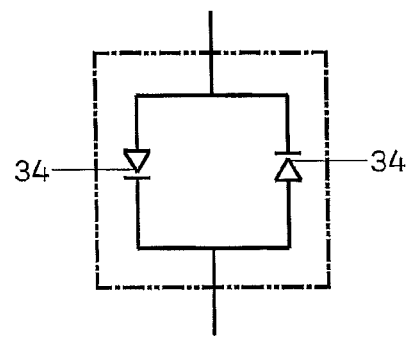

FIG. 8 shows the contact side of a patch in the form of multiple strips that can either be used as a single patch to treat an enlarged area or divided into several as desired; the patch is dimensioned to be attached around a limb in one case or, in a larger size, around the neck of a patient, and in either case to be held in place by Velcro;

FIG. 9A shows the external side of a patch in the form of multiple strips that can either be used as singly to treat an enlarged area, or torn or cut into single or multiple strips according to the area to be treated; the patch is arranged to be adhesively attached to a patient;

FIG. 9B shows diagrammatically a LED arrangement that can be used with the patch;

FIG. 10A illustrates various ways that a patch can be positioned to treat a patient; and FIG. 10B illustrates a patch comprising a pair of strips attached round a patient's wrist.

Figure 1A:
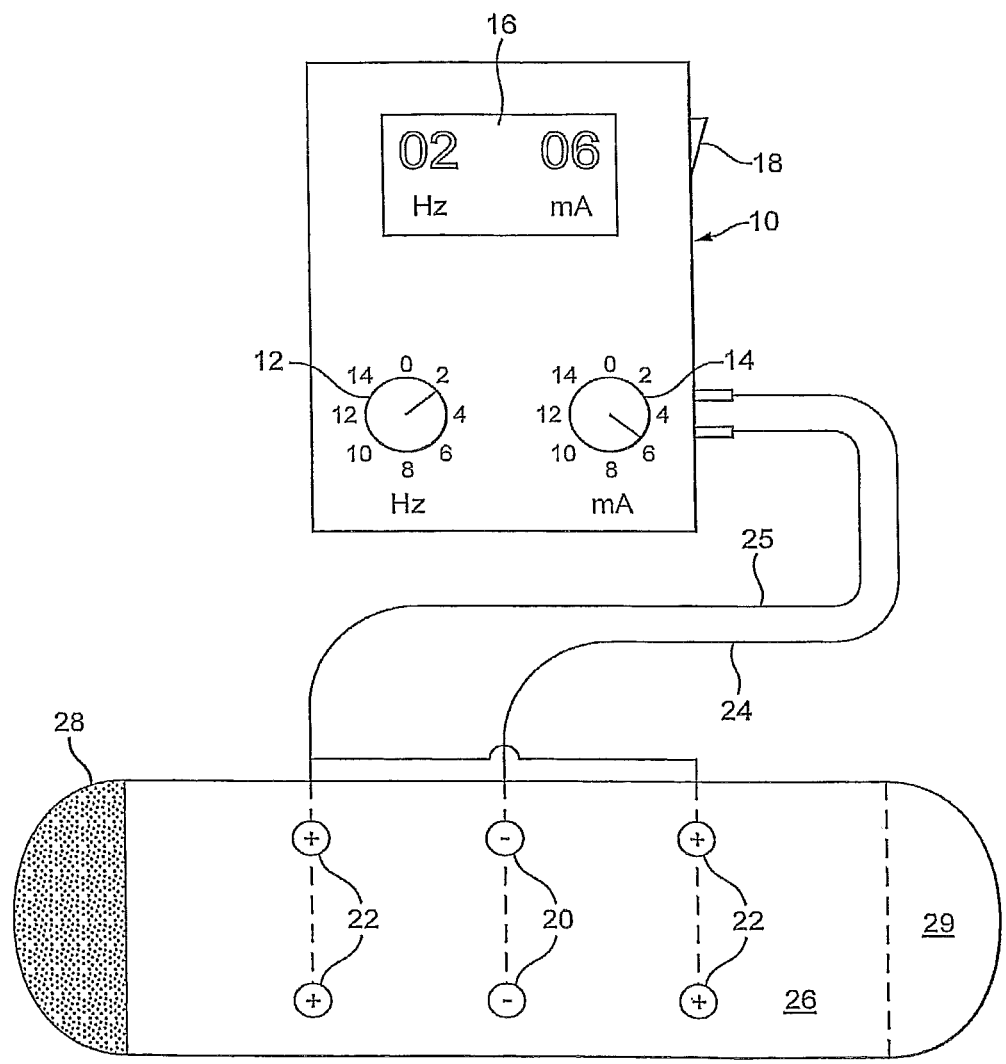
FIG. 1A is a diagrammatic view of a stimulating device where the electrodes are mounted on a flexible, semi-rigid band.

In FIG. 1A a stimulating device 10 which is controlled by a frequency button 12 and a power button 14. The output parameters are displayed on an LCD screen 16. An on/off switch is provided at 18.

The output from the device 10 is supplied by leads 24 to a patch 26 having two stud electrodes 20 identified as reference electrodes and four stimulating electrodes 22. Each of the electrodes 20,22 comprises a metal stud with a substantially hemispherical tip projecting from a semi-rigid but flexible patch 26 in the form of a band that can be attached firmly for example around a patient's wrist by means of a Velcro strip 28,29 at either end.

Figure 1B:
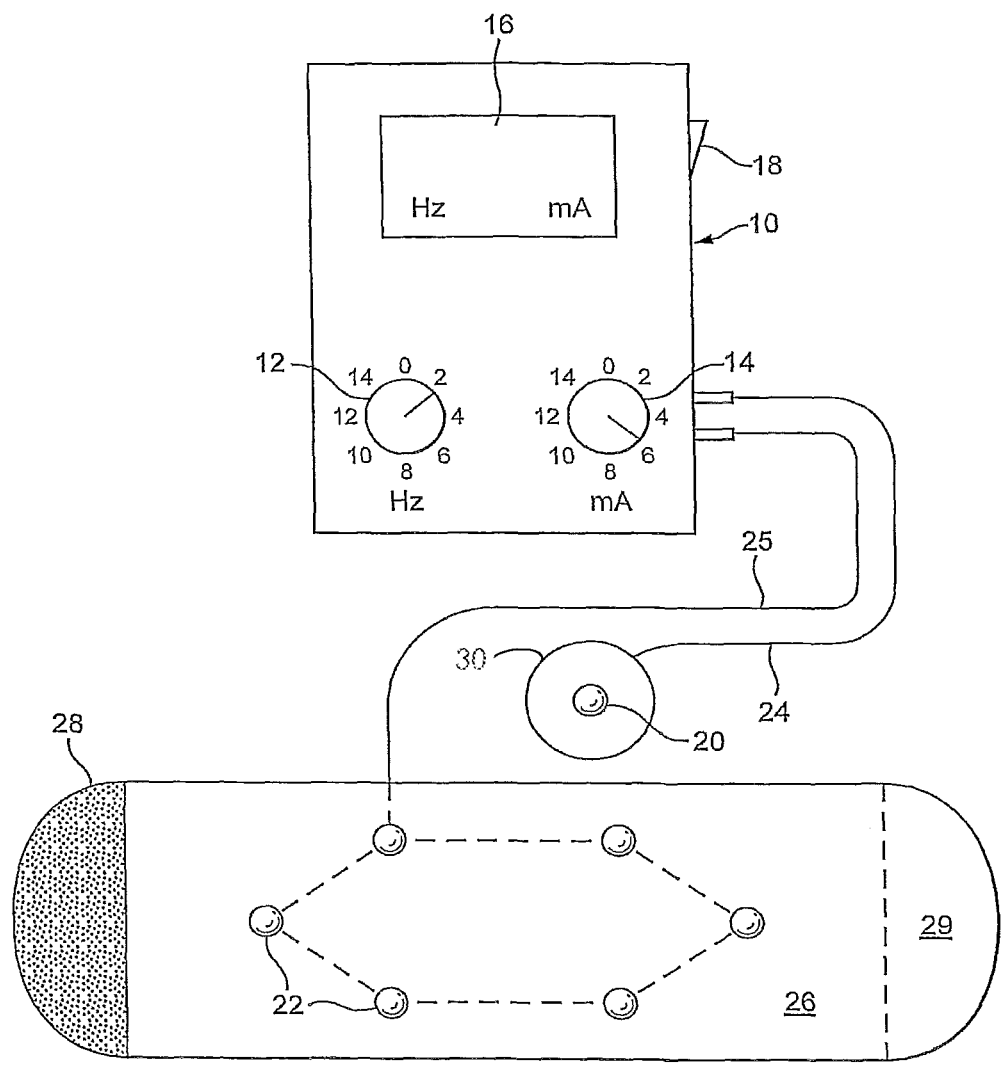
FIG. 1B is a diagrammatic view of a device similar to that in FIG. 1A, but where the reference electrode is in the form of a patch.

In FIG. 1A pair of reference electrodes 20 (cathodes) are connected to the stimulating device 10 by a lead 24, and the stimulating electrodes 22 (anodes) are connected by a lead 25. In FIG. 1B the reference electrode 20 is mounted on a separate silicone patch. The number of stimulating electrodes 22 and their spacing will be chosen by the specialist to suit the symptoms of the patient, generally by trial and error.

Each of the electrodes 20, 22 has a diameter of 4 to 8 mm and projects about 5 to 10 mm from the patch 26 formed of semi-rigid or stiff, insulating fabric material. They are fixed firmly to the patch so that when the latter is attached by means of a strap sufficient pressure can be applied to the electrodes to cause an indentation in the patient's skin, but not penetration.

For example, around a patient's chest, the electrodes should cause an indentation in the patient's flesh and are typically spaced apart by about 100 mm, though they may be customised as the exact required spacing will depend upon the diagnosis and the treatment prescribed by a practitioner.

In practice the centre pair of electrodes 20 (FIG. 1A) acts to produce a contact with the patient's skin as reference electrodes 20, whilst the others, or stimulating electrodes 22, are on either side of the reference electrodes 20. The reference electrodes may be located at the perceived centre of the point of pain in the affected area, in order to produce the optimum level of relief. The stimulating signal acts on both pairs of stimulating electrodes substantially simultaneously, or alternately. The effective area of the reference electrodes 20 may have to be enlarged to reduce the current concentration on the skin if it is intended to activate all the stimulating electrodes simultaneously.

In FIG. 1B the reference electrode 20 comprises a separate silicon-carbon patch 30 arranged to be attached to a patient's skin close to the affected area. A gel may be used to enhance the conductivity between the studs and the patient's skin, and similarly for the reference silicone gel. In FIG. 1B the stimulating electrodes 22, are arranged here in a hexagonal pattern of a short stems set into a semi-rigid support 26.

The patch 26 is in the form of a strap shown for attaching around a patient's wrist by means of a length of Velcro® 28 at one end which attaches to a corresponding gripper 29 on the other end of the strap. As an alternative, or a supplement to the Velcro attachment of the patch, its skin-side may be coated with an adhesive to enhance the available pressure on the studs.

The stimulating electrodes 22 on the patch 26 may be arranged in any desired pattern, such as one of those shown and described below with reference to FIG. 2. Once the electrodes have been correctly located, the patch 26 is attached firmly to hold the patch and the electrodes against the patient's skin whilst the stimulating signal is adjusted to provide the optimum level of relief whilst minimising any discomfort.

FIGS. 2A-C shows in plan various patterns that may be used for the electrodes 22 on the patch 26. FIG. 2A shows stimulating electrodes 22 in the shape of a simple square for use with a separate reference electrode (not shown). The dimensions are selected to fit the pain pattern of a patient; the distance d between adjacent electrodes may be from about 20 to 150 mm; 100 mm has been found to be very effective for the back or spine whilst the electrodes will be more closely spaced for smaller members, such as the hand, neck or eyes. Each electrode has a rounded contact end substantially in the form of a hemisphere.

FIG. 2B shows a circular or hexagonal array of stimulating electrodes 22 surrounding a central electrode 38 which may be used as the reference electrode. If a patch 26 as shown in FIG. 1 is used, the central electrode 38 will be another stimulating electrode activated with the other electrodes or in sequence. The central electrode 38 may also be used as a locating electrode in order to assist in locating the device. The radius r of the array or cluster will typically be about 100 mm.

FIG. 2C shows an elongated array of electrodes 22 for treating extended spinal pain. Generally up to 9 pairs of electrodes are sufficient to treat back pain, though more may be used if required.

This electrode array appears to produce good results for such larger sites and may be to about 100 mm in width and spaced apart by distance d which is typically 100 mm. Such larger electrode arrays may comprise up to 24 electrodes, but this may also call for multiple reference electrodes or one having a greater surface area if multiple stimulating electrodes are to be activated simultaneously.

FIGS. 3A and 3B show diagrammatically a patch in the form of or incorporated into a cap or headpiece 26 fitted with five pairs of stimulating electrodes 22 connected to the power supply 10. One or more reference electrodes 20 is also provided in the headpiece as required.

FIG. 4 shows diagrammatically a patch in the form of or incorporated into a glove 50 fitted with multiple electrodes 22 connected to a power source 10. In order to make the glove a standard item that can be adapted to as many patients as possible, a large number of stimulating electrodes 22 are provided which can be activated selectively as required to treat the patient's pain. In an alternative embodiment, not shown, the stimulating device may be incorporated into a small unit clipped onto the glove, and may be provided with wireless connectivity for adjustment and control purposes.

Similarly, FIG. 5 shows diagrammatically a patch in the form of a pair of eye shields 52 each fitted with 5 stimulating electrodes 22. The stimulating electrodes 22 can be activated as required from the power supply 10. The reference electrode may be attached separately to the patient, or make use of one or more of the electrodes on one or both of the eye shields.

Other forms of the device are possible. For example, many sufferers of acute pain have muscular or other disabilities which make it difficult for them to hold a stimulating device in a way that applies the appropriate pressure in the desired location. Thus an adhesive patch holding the stud electrodes firmly in place overcomes this problem, In use, the combination of the pressure and the, albeit small, low frequency stimulating current appears to have a remarkably beneficial effect in terms of the pain relief achieved.

The power button 14 of the power supply 10 is adjustable typically to provide a current up to the maximum of 60 mA. As described above, the frequency is varied by the frequency button 12. The pulse width may either be varied by means of another control (not shown) or varied automatically as a function of the applied current in order to optimise the applied power. For example, a stimulating pulse in the shape of a square-wave with a frequency of 15 Hz has a pulse with a duration of 0.7 milliseconds at a current of 12 mA may be suitable for treating pain in a wrist or hand. A higher power level (in Coulombs) may be required for back or spinal pain, and rather less for facial or eye pain. This appears to produce an effective treatment whilst enhancing battery life in the case of a portable device. Thus, the shorter the pulse and the lower the current, the longer the battery life.

As mentioned above in the introduction, the stimulating electrodes are located fairly accurately by means of a locating stimulator, or by using the stimulating device in its locating mode where a signal is sent to one or more of the stimulating electrodes in order to locate the pain to be treated. 'Fairly accurately' is a good enough indication of the region as often the patient may not be able to be very precise or specific, but because of the multiple stimulating electrodes incorporated in the stimulating device in accordance with the one or more embodiments, relief is provided over a larger area than with any other known device.

Once the pain has been located, the locating stimulator is removed, or the locating mode on the stimulating device is disabled. The chosen electrode array is then placed on the site of the pain and the various parameters of the stimulating signal are adjusted by a specialist while the patient indicates the optimum level of relief obtained.

Once the specialist is satisfied, he adjusts the settings of the power supply allowing for some margin and autonomy for the patient to make some minor adjustments to the settings in the light of his experience without further supervision. The patient is then free to use the device as often as he wishes in the knowledge that the device is safe. It is also small enough to be taken with him as required; the low power level used provides a high level of autonomy and independence in case the pain flares up unexpectedly.

Various embodiments are directed to the treatment of chronic pain and cosmetic applications that may avoid the need for an implanted device, with a non-invasive, multiple external treatment approach that is flexible and convenient.

FIGS. 6A and 6B (and an alternative in FIG. 6C) illustrate respectively a plan of the external surface and a centre cross-section of a patch 10 having a single stud 12 mounted on a semi-elasticated adhesive support 14, for use in the treatment of the Specified Conditions. In FIG. 6B the stud 12 has a smooth, substantially hemispherical form for contact with a patient's skin 20, and in FIG. 6C the stud has a rounded distal end where a lesser indentation is required or is sufficient to achieve the desired indentation in the patient's skin. The stud 12 has a flat backing washer 16 flush with the exterior surface of the support 14 in order to better transfer pressure from the support to the stud 12, and accordingly, in use, to the patient's skin.

In use, the patch is stretched and stuck by means of its adhesive surface 18 to the patient's skin in the desired location so that the hemispherical stud is pressed against the patient's skin due to the adhesive grip of the support 14.

(Note: in the drawings the adhesive surface of the support, and the stud(s), may not be shown as actually touching the skin, for clarity of illustration.) In use the adhesive grips the skin—with no gap between the two—so that the studs 12, aided by the backing washers 16, are pressed firmly into the skin; similar interpretation should be made where other means of attachment, e.g., a strap or Velcro, are used.

In practice the depth (from its rounded distal surface to its back in line with the backing washer 16) of the stud 12 (as in the other applications described below) will be chosen according to the diameter of the studs, the application to be treated and the desired pressure on the studs against a patient's skin required to achieve the benefit of the electrical stimulation. For applications where a deeper indentation is required, for example on the abdomen of an obese patient, the depth of the studs may need to be increased or the studs prolonged. Improved electrical conductance can be achieved by using a conducting gel.

Prior to the commencement of treatment, the stud 12 may be positioned for optimum effect using a stimulating signal applied to the stud or to a stimulating probe (not shown). The amplitude, frequency, pulse duration and length of each treatment will be determined by the patient's reaction to the initial stimulating signal and that applied in use to the stud 12.

The stud has an electrical connection 22 to a terminal or control unit 24. Where the patch is hard-wired to an external stimulating unit, it is connected via the terminal 24.

Alternatively a signal generator and power source are provided at 24 and form part of the patch or may be removably attached to it. The signal generator 24 incorporates a radio frequency transmitter so that the stimulating parameters can be pre-set by a physician or specialist external means as herein defined. Small adjustment and turning on and off may also be enabled for the patient to use a smart phone or tablet to control the patch.

An earthing patch or reference electrode may be provided on the sticky surface 18 of the support, or as a separate silicone gel electrode attached nearby (not shown). This is to be understood in respect of all the examples shown and described herein and with reference to the accompanying drawings. Where a plurality of electrodes is shown, some of the electrodes may be connected either to be used as reference electrodes or for the polarity to be alternated between electrodes, or for an external, suitably-dimensioned silica patch to be provided, or for a part of the adhesive surface of the support to comprise an earthing or reference electrode.

Generally the parameters of the stimulating signal will be set by a physician or specialist by hard wire or via an RF link so that the patient has no or only limited ability to alter the stimulating signal in amplitude or frequency. Where the patient is able to fine tune the stimulating signal this is achieved by means of an RF link to a cellular device, or by other external means as herein defined.

A timer may be incorporated so that the stimulation takes place at regular intervals. The lack of hard wiring to the device greatly improves its acceptance and convenience for the patient. The power source may be battery powered, rechargeable, or fed by RF means.

FIGS. 7A, 7B and 7D similarly show diagrammatically a patch 10 comprising a plurality of electrically-conducting hemispherical studs 12 projecting from an insulating support 14 to which the studs are attached or inserted with a formed or attached backing washer 16 similar to the one described with reference to FIG. 6 above. In FIG. 7D the rounded studs are shallower, and suitable for treatments where less indentation is required.

As in FIG. 6 each stud 12 that is to be used for the electrical treatment is provided with an electrical connection 22 linking it to a terminal or signal generator and power source at 24.

In use pressure is applied to the studs 12 in order to keep them in firm contact with the with the patient's skin; this in itself may produce significant relief. In order to enhance the relief, low, varied or high frequency electrical stimulation may be applied to the studs as detailed below. The combination of multiple electrical stimulation and firm pressure on the stud electrodes produces in many cases a significant relief of the pain that has been targeted, that may endure for hours, if not days.

FIG. 7C is a diagrammatic side view of a patch 10 having shallower studs 12 suitable for use in rectal, urological, gynaecological applications. The studs may be 8 to 10 mm in diameter, but only 3 or 4 mm high (from base to apex) so as to minimise discomfort. Equally, the support may be specifically shaped and adapted to its purpose. It has a suitable adhesive coating at 18 for achieving suitable adhesion to the patient's skin 20 and for the studs 12 to have adequate contact without damaging the tissue. This is an application where studs made of a softer plastics material with an electrically-conducting surface may be preferred over harder metallic studs.

FIG. 8 shows the under-side surface of a patch 10 similar to the one shown in FIG. 7. In this Figure, four studs 12 are shown, though there may be any number as required, and the support 14 may be dimensioned such that the device may be attached to and held firmly against, by means of Velcro grips at 30 and 30', a limb or the neck of a patient. In this example, the patch 10 is shown as forming one of three similar units, formed as a single patch. In use it may be employed as a single patch to treat a painful area, such as a patient's lower back, or may be cut down or torn along the markings or perforations 32 to form a double or single unit, as desired.

Where the patch comprised 4 electrodes, and is three units wide, it will typically measure 10 to 100 cm long, and each strip will be 2 or 3 cm wide. The reference numerals are those identifying similar items in FIGS. 6 and 7 and relate accordingly.

FIG. 9A shows the outer surface of a multiple adhesive device 10. FIG. 9B shows an LED arrangement as used to produce a light effect when a stud electrode receives a stimulating signal of either polarity.

Although the patch in FIG. 9A is provided with an adhesive surface on its underside from which the studs project, it is otherwise similar in dimensions and characteristics to the patch shown in FIG. 8. The two differences are that an LED 34 (or pair of LEDs in the case of an alternating polarity of the stimulating signal) is provided above one of the stud electrodes 12. Also an earthing or reference area 36, e.g. of a silicone gel, is provided on the underside of the support 14 and electrically connected to the terminal or stimulating unit at 24. As the device in FIG. 8, the patch may be used integrally as a unit, or cut or torn along the perforations 32 to provide a single or multiple units.

FIGS. 10A and 10B illustrate figuratively how single or multiple units of the patch 10 as described with reference to FIGS. 8 and 9 may be employed in practice on a patient.

Positioning of a patch and/or the studs may be refined by using a stimulating probe to locate the nerve and muscle locations so that the patches with the stud electrodes may be positioned appropriately on the support. Such patches may be moved to adapt to the patient's response to treatment, or to accommodate a new patient.

In general, selective rows of studs on the patch are arranged to carry a stimulating signal and return path electrodes allow for a completion of the electrical circuit. If desired the signal to the stimulating and return electrodes may be reversed, either alternately or in sequence or in an arbitrary fashion. The device may be moved if desired in order to optimise treatment or extend the area of treatment.

Alternatively, the return path connection may be applied to the patient by means of a conducting silicone carbon patch (not shown); in view of the larger number of stimulating electrodes the conducting area of the patch may be significantly greater than that of each of the stimulating electrodes in order to avoid an excessive localised current that could cause discomfort.

Whilst a number of different applications have been alluded to, aspects of the invention may be used in various forms where a formed insulating support with an array of studs may be adapted to fit the area to be treated.

For example, the insulating support may be adapted and formed for treatment of a specific location as described in the general description above.

In the device according to one or more embodiments, the power supply may be arranged to apply a locating pulse to one or more of the stud electrodes in order accurately to locate the relevant nerve group in a patient in order to maximise the relief to the patient yet using the smallest possible current.

The fact that the studs are arranged to be applied externally for non-invasive use permits the device to be used and, to a certain extent, controlled by a patient, although the initial set-up of the device will generally be performed by a medical practitioner or specialist. The very low current which has been found to be effective allows the device to be manipulated safely by older people—the most frequent sufferers from chronic pain—or even by children or people who are handicapped, without endangering them. Alternatively, the relief provided by the pressure of the studs may be sufficient to relieve the pain or discomfort, so that no electrical stimulation is required, or is required only infrequently.

Each stud may have a substantially hemispherical or parabolic shape with a diameter of 3 to 12 mm in diameter, or between 6 and 8 mm in diameter. In some applications smaller electrodes 4 to 6 mm in diameter are to be implemented, for example to provide a higher density of electrodes or for more delicate tissue. In areas where a more generalised relief is required, larger studs of diameter between 8 and 12 mm may be preferable.

The diameter of supporting washer or backing plate will generally be up to two or three times the diameter of the studs, say, 15 to 30 mm, or 20 to 25 mm, in diameter. It may equally be of a substantially elliptical, square, hexagonal or octagonal shape as may be dictated by the required application.

The invention claimed is:

1. An apparatus for treating a patient, the apparatus comprising:
    an insulating support;
    at least one rounded or substantially hemispherically-shaped or parabolically-shaped electrically-conducting stud projecting from one side of the insulating support, the at least one stud being configured and arranged with the insulating support to indent the patient's skin via the stud, in response to the insulating support being held against the patient's skin;
    a power source and a signal generator; and
    an electrical connector connected to the at least one stud and configured and arranged with the stud to connect the stud to the power source and the signal generator, the signal generator being configured and arranged with the electrical connector and the stud to
    in a locating mode, generate a first electrical stimulating signal at a first current level, therein facilitating location of a nerve region of the patient, and
    operate in a treatment mode, in response to locating the nerve region, by generating a second electrical stimulating signal at a second current level that is reduced relative to the first current level, therein facilitating stimulation of the located nerve region.

2. An apparatus for treating a patient, the apparatus comprising:
    an insulating support including a flexible strip, band or patch;
    at least one rounded or substantially hemispherically-shaped or parabolically-shaped electrically-conducting stud projecting from one side of the insulating support, the at least one stud being configured and arranged with the insulating support to indent the patient's skin via the stud, in response to the insulating support being held against the patient's skin;
    an electrical connector connected to the at least one stud and configured and arranged with the stud to connect the stud to a power source and to a signal generator of electrical stimulating signals; and
    for each stud, a stiff or rigid surrounding backing plate or washer configured and arranged to support the stud and having a diameter that is greater than the diameter of the stud and less than 3 times the diameter of the stud.

3. The apparatus of claim 2 in which the insulating support comprises an elasticated fabric having an adhesive surface on the side from which the at least one stud projects, the elasticated fabric being configured and arranged to stretch over the patient's skin in an area to be treated and to conform the apparatus to the area to be treated with the at least one stud held and exerting pressure against the patient's skin.

4. The apparatus of claim 2, further including the power source and the signal generator mounted on the insulating support and connected to the stud(s) via the electrical connector.

5. The apparatus of claim 4 in which the signal generator is configured and arranged to be controlled or adjusted by an external input.

6. The apparatus of claim 2 in which the at least one stud has a diameter of one of between 3 and 6 mm and between 8 and 12 mm.

7. The apparatus of claim 2 in which the insulating support comprises an elongated strip having three or more studs, the strip being configured and arranged with regions that promote separation of portions of the strip at predefined locations for cutting of the strip to a desired length for an intended application.

8. The apparatus of claim 2 in which the insulating support comprises several parallel strips each having a plurality of electrodes, the strips being configured and arranged for implementation either to be used as a single, multi-strip support, or to be torn or cut to form discrete strips for separate applications via regions of the insulating support that promote separation of the parallel strips at predefined locations, each location utilising one or more strips.

9. The apparatus of claim 2 in which the insulating support comprises a band, strip, belt or bracelet configured and arranged for attachment around a limb, wrist, ankle, head or torso of a patient and to bring the at least one stud into and maintained in contact with the patient's skin.

10. The apparatus of claim 2, wherein
    the at least one stud includes at least two studs, and
    the insulating support is configured and pre-formed so as to fit closely around a part of a patient's anatomy where treatment is to be applied, and is configured and arranged with the at least two studs to hold and maintain the respective studs in firm contact with the patient's skin along differently-aligned surfaces of the skin.

11. The apparatus of claim 2 in which the insulating support and the at least one stud have interlocking hook-and-loop fasteners configured and arranged to engage with one another via the hooks engaging with the loops and to secure the at least one stud and the insulating support to one another.

12. The apparatus of claim 2 in which the insulating support has an interlocking hook-and-loop fastener configured and arranged to engage another hook-and-loop fastener on the patient to secure the insulating support to the patient.

13. The apparatus of claim 2 in which the insulating support comprises a formed pad or device configured and arranged to treat rectal, urological or gynaecological pain, by conforming to regions of a patient's anatomy and wherein the electrically-conducting stud includes a compliant material base configured and arranged to flex upon contact with the patient and a conductive surface on the base and configured and arranged to interface with the patient's anatomy.

14. The apparatus of claim 2 in which the insulating support comprises a shell configured and arranged to clip or clamp around a part of a patient's anatomy that is to be treated.

15. The apparatus of claim 2 in which the at least one stud has a diameter of between 4 and 10 mm.

16. The apparatus of claim 2 in which the at least one stud has a diameter of between 6 and 8 mm.

17. An apparatus for treating a patient, the apparatus comprising:
   an insulating support;
   at least one rounded or substantially hemispherically-shaped or parabolically-shaped electrically-conducting stud projecting from one side of the insulating support, the at least one stud being configured and arranged with the insulating support to indent the patient's skin via the stud, in response to the insulating support being held against the patient's skin;
   an electrical connector connected to the at least one stud and configured and arranged with the stud to connect the stud to a power source and to a signal generator of electrical stimulating signals; and
   one or more light emitting diodes operable with the electrical connector so that in use a patient can visually identify when an electrical stimulating signal is being applied to the at least one stud or to selected studs.

18. A method for treating a patient, the method comprising:
   applying at least one electrically-conducting stud mounted on an insulating support with a stiff or rigid surrounding backing plate or washer configured and arranged to support the stud and having a diameter that is greater than the diameter of the stud and less than 3 times the diameter of the stud, the stud being rounded or substantially hemispherically-shaped or parabolically-shaped, the stud projecting from one side of the insulating support;
   indenting the patient's skin via the stud by holding the insulating support against the patient's skin; and
   applying an electrical stimulating signal to the at least one stud at a frequency within a range 1 to 50 Hz or 5 kHz to 10 kHz and a current in a range 0.2 mA to 60 mA, using a power source and a generator of the electrical stimulating signals that is connected to the stud by an electrical connector.

19. The method of claim 18 in which the electrical stimulating signals have pulse width from 0.05 to 1 ms.

20. The method of claim 18, wherein the electrical stimulating signal is in the frequency range 2 to 10 Hz.

21. The method of claim 18 wherein the electrical stimulating signal is in the frequency range 5 to 10 kHz.

22. The method of claim 18 wherein the current of the electrical stimulating signal is in the range 2 to 10 mA.

23. The method of claim 18 wherein the at least one stud is located on the patient by applying a stimulating signal to pre-determine an optimum position for treatment.

24. The method of claim 18, wherein applying the electrical signal includes:
   in a locating mode, locating a nerve region of the patient by generating a first electrical stimulating signal at a first current level, and
   in response to locating the nerve region, operating in a treatment mode and generating a second electrical stimulating signal at a second current level that is reduced relative to the first current level, therein facilitating stimulation of the located nerve region.

25. The method of claim 18, further comprising holding and maintaining the studs pressed firmly against the skin of a patient using a mechanical component during a period of treatment.

* * * * *